(12) United States Patent
Sindi (10) Patent No.: US 7,740,803 B2
(45) Date of Patent: Jun. 22, 2010

(54) BIOCHEMICAL SENSOR WITH THERMOELASTIC PROBES

(75) Inventor: Hayat Sindi, Cambridge (GB)

(73) Assignee: Sonoptix (UK) Limited, London (GB)

( * ) Notice: Subject to any disclaimer, the term of this patent is extended or adjusted under 35 U.S.C. 154(b) by 1218 days.

(21) Appl. No.: 10/528,554

(22) PCT Filed: Sep. 22, 2003

(86) PCT No.: PCT/GB03/04153

§ 371 (c)(1),
(2), (4) Date: Aug. 17, 2005

(87) PCT Pub. No.: WO2004/027396

PCT Pub. Date: Apr. 1, 2004

(65) Prior Publication Data

US 2006/0148092 A1    Jul. 6, 2006

(30) Foreign Application Priority Data

Sep. 21, 2002  (GB) ................. 0221966.5

(51) Int. Cl.
*G01N 33/00*  (2006.01)
*G01N 15/06*  (2006.01)
*G01N 33/48*  (2006.01)

(52) U.S. Cl. .............. 422/68.1; 436/134; 356/432

(58) Field of Classification Search ........... 422/68.1; 436/134; 356/432
See application file for complete search history.

(56) References Cited

U.S. PATENT DOCUMENTS

| 4,513,384 A | 4/1985 | Rosencwaig |
| 4,679,946 A | 7/1987 | Rosencwaig et al. |
| 5,479,259 A | 12/1995 | Nakata et al. |
| 5,633,724 A | 5/1997 | King et al. |
| 5,829,437 A | 11/1998 | Bridges |
| 5,874,219 A | 2/1999 | Rava et al. |

(Continued)

FOREIGN PATENT DOCUMENTS

DE    19836110    2/2000

(Continued)

OTHER PUBLICATIONS

Mittleman et al., "Recent advances in terahertz imaging", Appl. Phys. B (1999), pp. 1-10.

(Continued)

*Primary Examiner*—Sam P Siefke
*Assistant Examiner*—Bryan T Kilpatrick
(74) *Attorney, Agent, or Firm*—Fish & Richardson P.C.

(57) ABSTRACT

The thermoelastic response of certain materials to an incident electromagnetic excitation beam is highly sensitive to physical conditions existing at the surface of the material. Probe structures carrying probe materials are used as sensors in the analysis and investigation of biochemical molecules. Each probe structure is adapted to undergo a thermoelastic response when excited by temporally varying electromagnetic radiation, characteristics of the thermoelastic response being a function of physical properties of material binding to the surface of the probe structure. An electromagnetic excitation means directs electromagnetic energy at a selected one of the probe structures in order to elicit the excitation response. A detection means determines change in excitation response of the probe structures resulting from the binding of molecules thereto.

41 Claims, 9 Drawing Sheets

U.S. PATENT DOCUMENTS

| | | | |
|---|---|---|---|
| 5,907,408 A * | 5/1999 | Naya et al. | 356/445 |
| 5,934,150 A | 8/1999 | Srinivas et al. | |
| 5,936,150 A | 8/1999 | Kobrin et al. | |
| 6,046,056 A | 4/2000 | Parce et al. | |
| 6,051,380 A | 4/2000 | Sosnowski et al. | |
| 6,061,589 A | 5/2000 | Bridges et al. | |
| 6,111,652 A | 8/2000 | Melendez et al. | |
| 6,159,681 A * | 12/2000 | Zebala | 435/4 |
| 6,373,577 B1 | 4/2002 | Brauer et al. | |
| 6,438,497 B1 | 8/2002 | Mansky et al. | |
| 6,600,563 B1 * | 7/2003 | Bahatt et al. | 356/445 |
| 2003/0090663 A1 * | 5/2003 | Autrey et al. | 356/432 |
| 2003/0210399 A1 | 11/2003 | Bahatt et al. | |
| 2004/0180369 A1 * | 9/2004 | Franzen et al. | 435/6 |

FOREIGN PATENT DOCUMENTS

| | | |
|---|---|---|
| EP | 0 352 789 | 1/1990 |
| EP | 0 366 151 | 5/1990 |
| EP | 0 369 176 | 5/1990 |
| EP | 0 459 613 | 12/1991 |
| EP | 1 546 682 | 2/2010 |
| GB | 2 204 408 | 11/1988 |
| GB | 2 244 557 | 12/1991 |
| WO | WO 97/29362 | 8/1997 |
| WO | WO 98/10288 | 3/1998 |
| WO | WO 99/03684 | 1/1999 |
| WO | WO 9930135 A1 * | 6/1999 |
| WO | WO 00/10011 | 2/2000 |
| WO | WO 01/57498 | 8/2001 |
| WO | WO 03/042668 | 5/2003 |
| WO | WO 03/042669 | 5/2003 |
| WO | WO 03/042690 | 5/2003 |
| WO | WO2004/027396 | 4/2004 |

OTHER PUBLICATIONS

International Search Report in Application No. PCT/GB2003/004153, dated Apr. 3, 2004.

Examination Report in Application No. GB0221966.5, dated Jun. 13, 2003.

Tatsuma et al., "Multichannel quartz crystal microbalance", Analytical Chemistry, vol. 71(17), pp. 3632-3636 (Jul. 1999).

Reply to Communication of Nov. 23, 2007, in EP Application No. 03748331.0, dated Mar. 18, 2008.

Communication in EP Application No. 03748331.0, dated Nov. 23, 2007.

Reply to Communication of Apr. 27, 2006, in EP Application No. 03748331.0, dated Oct. 26, 2006.

Examination Report in EP Application No. 03748331.0, dated Apr. 27, 2006.

Reply to Communication of Sep. 30, 2005, in EP Application No. 03748331.0, dated Apr. 6, 2006.

Examination Report in EP Application No. 03748331.0, dated Sep. 30, 2005.

* cited by examiner

Interferometer & oscilloscope detector

*Fig. 5A*

Interferometer & Lock in amplifier detector

*Fig. 5B*

Piezo-crystal & oscilloscope detector

*Fig. 5C*

Piezo-crystal & Lock in amplifier detector

*Fig. 5D*

Fig. 6A Oscilloscope detector output (high resolution)

Fig. 6B Oscilloscope detector output

Fig. 6C Frequency spectrum

Fig. 7A

Fig. 7B — Protein A (250ug/ml) / Protein A + anti Protein A (250ug/ml) — Protein A-anti Protein A Fig. 7C — Poly C (500ug/ml) / Poly C + Poly G (500ug/ml) — Poly C – Poly G

BIOCHEMICAL SENSOR WITH THERMOELASTIC PROBES

The present invention relates to a transducer sensor device, and in particular to an array of such devices that can be used in the analysis of molecular structures, e.g. of bio-chemicals.

For the efficient analysis and investigation of biochemical molecular structures, such as that which occurs during DNA sequencing, there is a strong demand for analytical tools that enable the use of hundreds or even thousands of molecular probes substantially simultaneously.

One way of achieving this is to provide a substrate with a large number of different probe molecules bound to its surface in an array. Each probe molecule is adapted to bind with a selected target molecule in a sample under analysis. The sample is first provided with suitable fluorescent markers prior to exposure to the array of probe molecules. After exposure of the sample to the array, provided that the location and identity of each different probe molecule in the array is known, analysis of the sample is possible using a confocal microscope to identify array positions in which fluorescence indicates the presence of a sample molecule bound to the respective probe molecule.

Typically the probe molecules are oligonucleotides and the sample under analysis is a DNA sequence. Using such fluorescent techniques relatively high probe densities are possible.

A disadvantage of such techniques is that the sample must be pre-treated with fluorescent markers to allow for fluorescence detection after exposure to the probe array. A further disadvantage is that microscope imaging systems can be costly and inconvenient for rapid analysis.

Surface plasmon resonance (SPR) is based on an optical phenomenon that occurs in a thin metal film at an optical interface under conditions of total internal reflection. Conventional SPR sensors use a prism 'device' coated with a single thin metal layer. Any chemical adsorption to the outer surface of the metal layer or to an immobilised antibody or ligand on the outer surface of the metal layer leads to interfacial changes in the refractive index of the film. By directing a light beam into the prism, it is possible to measure the reflected light as a function of intensity and angle, to produce the well known SPR resonance spectrum. In a recent extension of this concept (U.S. Pat. No. 6,373,577) planar waveguide elements coated with a thin metal film are organised as a linear array of elements in which SPR can be separately generated.

The present invention is directed to an improved system and apparatus for analysing a sample using one, or an array, of probes that does not require the use of markers, that does not involve SPR, and that can readily be implemented using low cost equipment. In contrast to SPR, the present invention is based on a high peak power beam of electromagnetic radiation which temporarily illuminates a small region of a thermoresponsive sensor, such as a thin metal layer. The incident angle of the beam is constant and the electromagnetic radiation induces a thermal response that can be detected with an appropriate transducer. Chemical adsorption to the surface modulates the thermal response, which in turn affects the electrical output of the transducer.

According to one aspect the present invention provides an apparatus for detecting a variation in a probe, comprising:

a probe which is adapted to undergo one or more of a thermoelastic, thermoelectric or thermomagnetic excitation response when excited by temporally varying electromagnetic radiation, the excitation response being a function of the physical and/or chemical properties of the probe and/or of material binding thereto;

a source of electromagnetic radiation;

means for directing the electromagnetic radiation at the probe; and a transducer adapted to determine the excitation response of the probe.

The probe usually comprises a plurality of probe molecules (probe material) carried on a separate surface, e.g. the surface of a substrate. The substrate is preferably a thin film. However where the probe material on its own possesses appropriate physical properties the probe may be such material on its own.

We prefer the apparatus to comprise a plurality of probes, e.g. in the form of an array. Each probe may comprise probe material which is different to that on other probes.

The probe material may consist of a collection of the same molecules or of a mixture of different molecules.

The surface of the probe may be a flat, e.g. a flat plate, but the surface may also be curved, e.g. a segment of a sphere and such curved surfaces are included in the term "plate".

The thermal excitation response may be thermoelectric, thermomagnetic or preferably thermoelastic.

Preferably the source of electromagnetic radiation emits radiation in the optical portion of the electromagnetic spectrum, and more preferably is a laser. The source of electromagnetic radiation may be positioned so that the radiation impinges directly on the probe material, but more usually is positioned so that it first passes through a substrate transparent to the radiation before impinging on the probe material.

According to another aspect the invention provides a sensor, comprising:

a substrate, and one or more probes on the surface of the substrate, the probes being adapted to undergo one or more of a thermoelastic, thermoelectric or thermomagnetic excitation response when excited by temporally varying electromagnetic radiation, the excitation response being a function of the physical and/or chemical properties of the probe(s) and/or material binding thereto.

The sensor is preferably in the form of a plate.

The substrate is preferably electromagnetically transparent, and may act as, or be part of, a transducer. The substrate is conveniently of such a thickness that it has sufficient strength for ease of handling, and also that it will permit the desired amount of electromagnetic radiation to pass through it. A convenient thickness is generally in the range 0.2 to 1.0 mm.

Preferably the sensor includes:

a plurality of probes, e.g. thin film probe structures as defined below, each of which is adapted to undergo a localised electrical response when the probe is excited by temporally varying electromagnetic radiation and of generating an electrical output response corresponding thereto, the characteristics of the electrical response being a function of the physical or chemical properties of the probe and/or of material binding thereto, and a transducer for transmitting the electrical response.

Preferably different probe materials are bound to different probes. When the probes comprise probe materials bound to a separate surface we prefer the surface to carry a layer, and preferably a thin layer, e.g. of silica, for receiving the respective probe materials and assisting the probe materials to adhere to the surface. The layer may, for example, be about 10 nm thick In one aspect the present invention utilises the phenomenon that the thermoelastic, thermoelectric or thermomagnetic response of a probe can be highly sensitive to physical and/or chemical conditions existing at the surface of the probe. Indeed it has been shown that the thermoelastic (acoustic) response characteristics can vary substantially as a function of mass bound to a surface, surface stiffness, dielectric constant, viscosity, surface free energy and other general surface properties.

The present invention exploits this phenomenon by, for example, providing one or more independent locations (spots or dots) on a substrate surface for which the thermal (e.g. thermoelastic) response can be assessed either qualitatively or quantitatively. When more than one location is involved the response characteristics can be assessed separately. The locations are preferably formed as an array of probes, the array preferably having a density of between 100 and 1,000,000 locations per square centimeter, and more preferably between 100 and 100,000 locations per square centimetre. Each location in the array effectively provides an independently addressable probe. Each probe can be excited to generate the thermal response by way of a beam of electromagnetic radiation, e.g. a laser beam.

Under an electromagnetic, e.g. laser, beam the probes absorb energy, e.g. optical energy, which is converted into thermal energy, which may be vibrational or acoustic energy, referred to herein as a thermoelastic response. The periodic signal derived from a pulsed laser is ideal for linking high performance detection circuits that are based on synchronous detection thus providing a high signal to noise ratio. Short nano or sub-nano second heating of the probe produces a localised volumetric expansion in the probe as a function of its density, thermal expansion coefficient and reflection coefficient.

Where the probe has one or more molecules derived from the sample to be analysed attached, e.g. chemically immobilised, bound or otherwise fixed thereto, the localised volumetric expansion will be modulated by the attached molecules thereby providing a differential thermoelastic expansion. This modulation in the thermoelastic response is used in the present invention.

By means of this invention very small probes can be used and in consequence attachment of even a small amount of sample to the probe will cause a relatively great change in the properties of the probe and thus provide a high degree of sensitivity.

Embodiments of the present invention will now be described by way of example with reference to the accompanying drawings, in which like numerals denote like parts, and.

Figure 1:
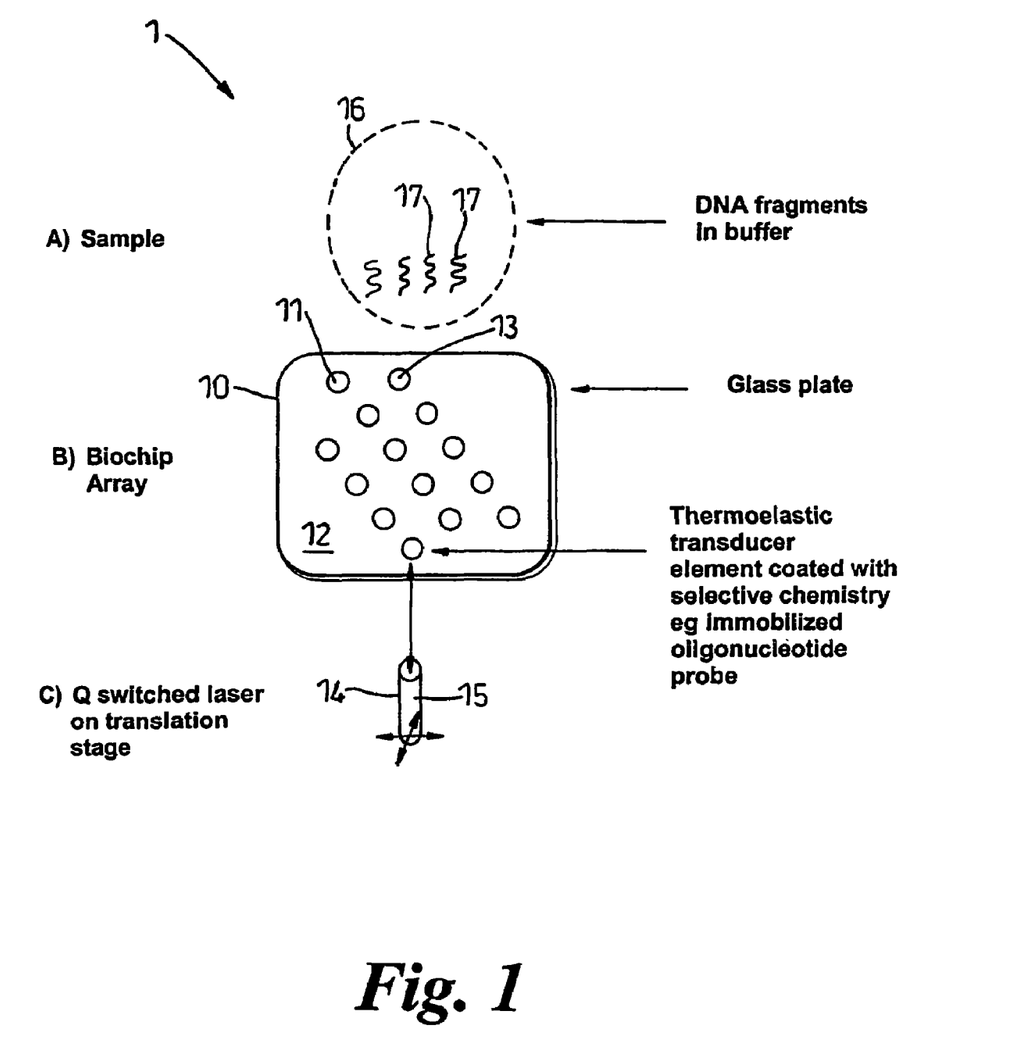
FIG. 1 is a schematic diagram illustrating the principles of the present invention.

With reference to FIG. 1, a transducer apparatus 1 for detecting spatially localised variations in material binding to a substrate is shown. A substrate 10, preferably formed from glass or similar material, has one or more thermoelastic sensing thin film structures 11 attached to the top surface 12 of the substrate in a conveniently configured array. Each of the sensing structures 11 has probe material 13 attached to the exposed upper surface of the thermoelastic thin film structures. The thin film structures will hereinafter be referred to as probe structures.

Preferably the probe structures 11 comprise dots or spots of any suitable shape having a surface area of approximately $10^{-6}$ to $10^{-5}$ square centimeters. In a preferred embodiment the probe material comprises an oligonucleotide adapted to bind with specific DNA fragments. Each probe structure, or group of probe structures, has different oligonucleotide probe materials bound thereto.

In the present embodiment, the substrate 10 is optically transparent, and positioned beneath it is an optical source 14, e.g. a Q-switched laser, for delivering an excitation signal to the probe structure through the thickness of the substrate. Together with the optical source is an optical detection system 15 for detecting modulations in optical radiation reflected or returned from the probe structures. The excitation and detection systems are displaceable relative to the substrate, preferably in a plane substantially parallel to the substrate, and optionally also relative to each other, to enable scanning of the array.

A sample 16 comprising a plurality of fragments 17, e.g. DNA fragments in a buffer solution, is brought into contact with the top surface 12 of the substrate where specific fragments 17 bind with specific probe material 13. The binding of the sample 16, 17 with the probe material 13 of specific probe structures 11 results in a change in the characteristics of the thermoelastic response induced in the probe structures and this change is detected using the excitation and detection systems 14, 15.

Excitation and Detection

Figure 2:
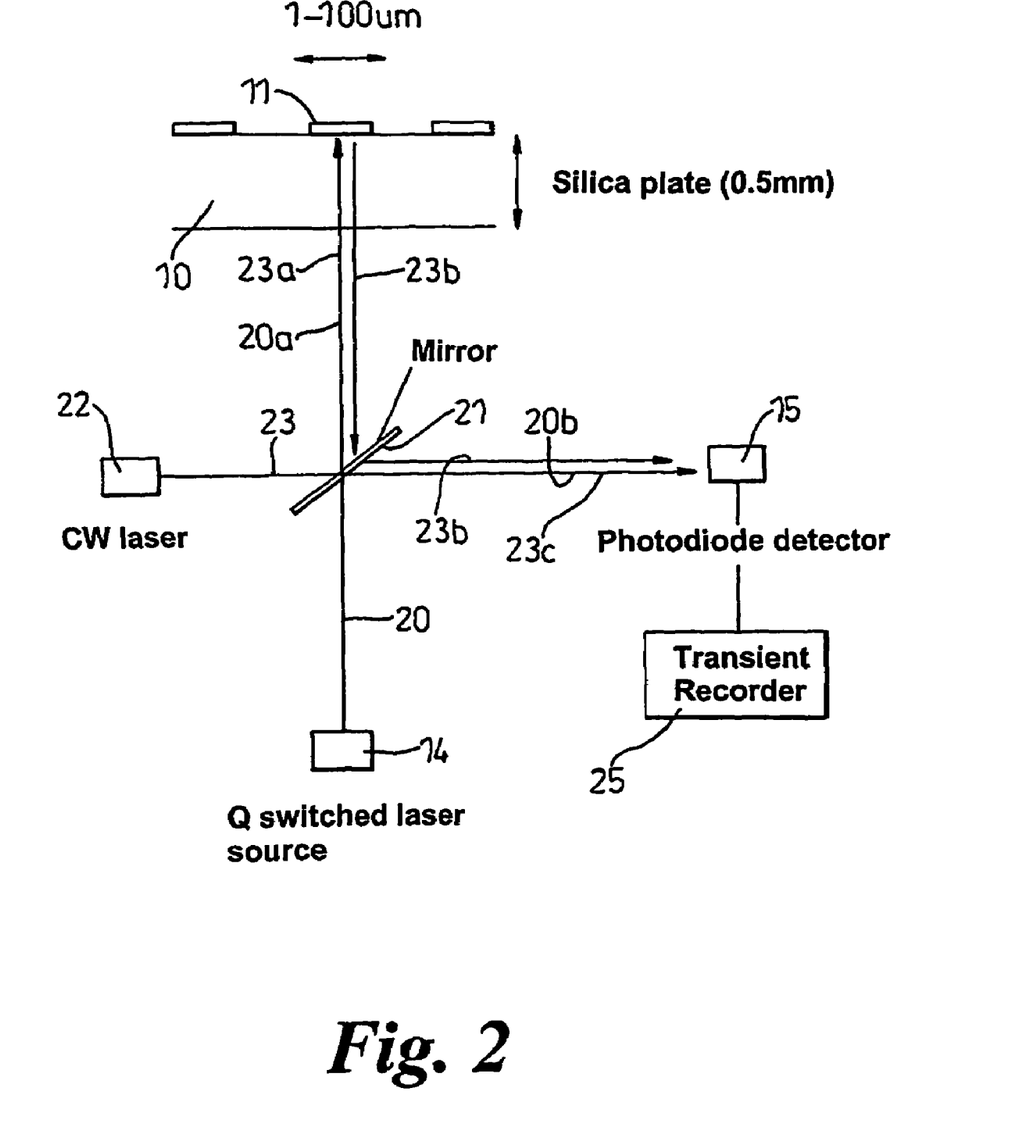
FIG. 2 is a schematic diagram of a first embodiment of the invention using a laser based excitation system and an optical detection system.

With reference to FIG. 2 a preferred arrangement of excitation and detection system will now be described.

A laser source 14 delivers an excitation beam 20 of suitable wavelength (e.g. 1056 nm) to a beam splitter 21. A first portion 20a of the excitation beam is transmitted by the beam splitter 21 to the substrate 10, and a second portion 20b is dissipated at the detection system 15. The first portion 20a of the excitation beam impinges on the substrate 10, is transmitted through the substrate and directed onto a selected probe structure 11.

A detection beam 23, from a continuous, low powered laser source 22 is also directed to the beam splitter 21. A first portion 23a of the detection beam is reflected by the beam splitter to the substrate 10 where it is reflected from the probe structure and deflected to the detection system 15 as an interference beam 23b. A second portion 23c of the detection beam is transmitted to the detection system directly as a reference beam. Interference between the two detection beam paths 23b and 23c occurs and this interference is detected by the detection system 15. The detection beam 23b is preferably broader than the probe structure so that it can detect excitation over the whole of the probe structure.

In this exemplary embodiment the probe structure 11 preferably comprises a metal film of thickness approximately 10 to 500 nm (and more preferably 10 to 100 nm), and having a diameter of approximately 1 to 100 μm. Alternatively the individual probe structures may be defined within a continuous film with the probe area effectively defined by the excitation beam area.

The probe structure may be formed from any suitable metallic or other materials that provides the requisite thermoelastic properties, and which permits binding of suitable probe materials thereto, or chemical modification for attachment of suitable probe materials. Preferred for ease of chemical attachment is gold, and for its thermoelastic properties is aluminium. Other suitable materials include silver, titanium, copper, tungsten and polymeric materials.

A proportion of the excitation beam 20a is absorbed by the probe structure 11 causing a thermoelastic volume change in the probe structure. This volume change results in one or more of a change in the thickness, area or position of the probe structure 11. For example, the excitation beam produces longitudinal waves in the probe structure 11 driven by localised heating of the metal.

In a preferred arrangement, the power density of excitation beam falling onto the substrate is of the order of $3 \times 10^{11}$ $W.m^{-2}$ and this power density yields a maximum strain on the probe structure of about 2%, ie. the width or thickness of the thermoelastic film increases by this amount. Generally, the minimum power density required of the excitation beam will depend upon the minimum thermoelastic response measurable by the detection apparatus. In a present embodiment, this minimum power density of excitation beam would be of the order of $3 \times 10^8$ $W.m^{-2}$.

The interferometer formed from the combination of a. the beam 23a that is reflected off the probe structure 11 as beam 23b, with b. the reference beam 23c operates between the short duration pulses of the excitation beam. The thermoelastic change in dimension of the probe structure results in a corresponding amplitude, phase and phase angle variation at the photodiode detector 15. The position and expansion of the probe structure 11 is a function of the probe material bound thereto (and/or of any sample material which is attached to the probe material).

The result is that the amplitude, phase and phase angle of the response to excitation measured at the photodiode 15 is directly related to the quantity of material bound to the probe structure 13. Similarly any storage of energy in the probe structure results in vibrational, e.g. acoustic, resonance, that decays with time and, to a first approximation, is inversely proportional to the quantity of material bound to-the probe structure 13, as will be shown later in FIG. 6.

In general terms the thermoelastic response of the probe structure due to the electromagnetic, e.g. laser, excitation results in a change in how the probe structure reflects light. Changes in the thermal response will occur as a function of any changes that occur to the physical and/or chemical properties of the material bound to the surface of the probe structure, which can be detected by the detection system 15. If the excitation response is initially measured for the probe structure with the probe material 13 bound thereto (calibration data), and is then re-measured after exposure of the probe material to the sample 16 (sample data) any changes to the physical and/or chemical properties of the material (e.g. any fragments 17) binding to the surface of the probe structure will be indicated, e.g. quantitatively, by the magnitude of change in the thermal response. For certain analytical purposes a qualitative response may be sufficient.

The data for sample 16 is acquired by the difference between the calibration data and the sample data. Fast analogue to digital converters (for example, a transient recorder 25 such as a digitising oscilloscope) translate this information into a series of digital waveforms for analysis by available software. Recording and storing data from the interactions of known probe materials on the probe structures with known fragments in a sample enables the rapid identification of such fragments in samples of unknown composition. An advantage of a wideband waveform acquisition system, e.g. an oscilloscope, is that the time domain signal is a fall record of the excitation from its initial motion to its eventual relaxation. Where a less detailed emission response is required it is possible to use a low frequency synchronous approach, e.g. a lock-in amplifier which is simple in form and does not require radio frequency components.

Those skilled in the art will recognise that the thermoelastic response may be measured in a number of ways.

The excitation energy of the laser 14 may be in the form of a single pulse (e.g. where only qualitative data is required), or a series of pulses (e.g. where quantitative data is required). For each pulse the induced stress response of the probe structure to the rising edge of the excitation pulse may be analysed from the received signal and displayed on an oscilloscope (not shown).

Alternatively the Q-switching rate of the excitation laser may be used to synchronise a lock-in amplifier in order to provide an enhanced signal to noise ratio.

Figure 3:
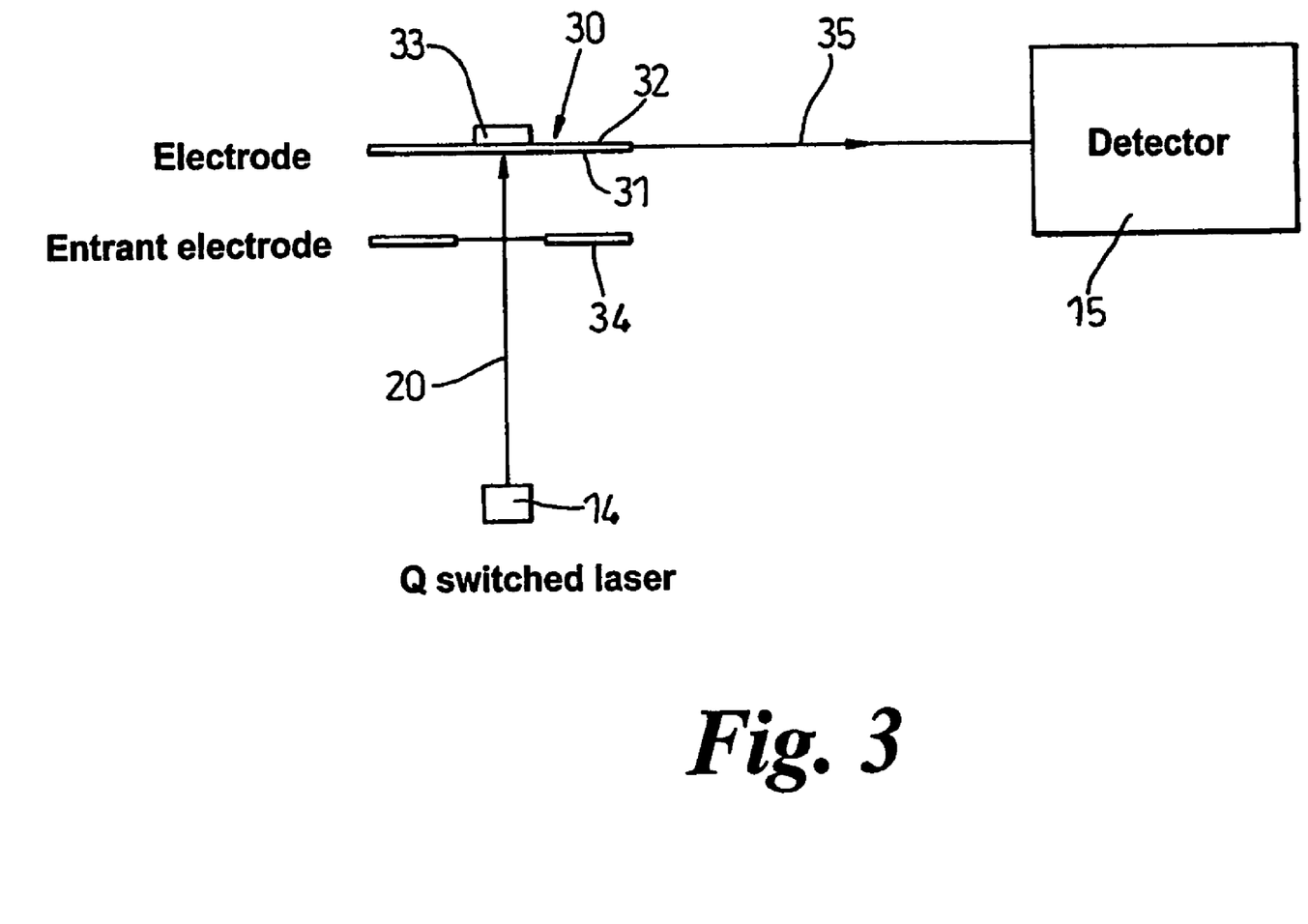
FIG. 3 is a schematic diagram illustrating a further embodiment of the invention using a laser based excitation system and a piezoelectric detection system.

With reference to FIG. 3 an alternative embodiment of probe structure, excitation system and detection system will now be described. In this arrangement each probe structure 30 is formed in a continuous thin film 32 of electrically conductive, thermoelastic material on top of a dielectric, optically transparent substrate 31. The thin film 32 can provide an upper electrode of a piezoelectric transducer. Preferably the optically transparent substrate is quartz.

In a preferred arrangement, a lower electrode 34, formed on the lower surface of the substrate 31 is an optionally apertured entrant electrode which provides access for an excitation beam 20 to the probe structure 30. The entrant electrode comprises a film of suitable electrically conductive material to provide a ground plane and thereby reduce external electromagnetic interference. The size of the probe structure 30 may therefore be effectively determined by the dimension of the excitation beam 20. If the entrant electrode is formed from an optically transparent electrically conducting material, e.g. an indium/tin oxide composition, then no aperture need be formed.

The electromagnetic excitation beam 20 in this instance comprises an optical beam generated by a Q-switched laser 14 and is preferably of the order of 1.0 to 100 μm wide. The probe structure 30 responds to incidence of the optical excitation beam by thermoelastic volume changes therein according to the intensity and location of the beam. This produces a vibrational, e.g. an acoustic, response in the probe structure 30 which induces movement in the adjacent piezoelectric substrate 31 and thereby produces a signal current 35.

The result is that vibration induced in the probe structure 30 is coupled into the substrate 31. A wide range of frequencies is generated as a high frequency current.

It will be understood that in this embodiment the thermoelastic response of the probe structure 30 due to laser excitation results in a modulation of the electronic properties of the probe structure, e.g. it will drive the thermoelastic excitation response. Changes in this thermoelastic response will occur as a function of any changes that occur to the physical and/or chemical properties of the material binding to the surface of the probe structure, which can be detected by an electrically based detection system, rather than an optically based detection system.

Figure 6A:
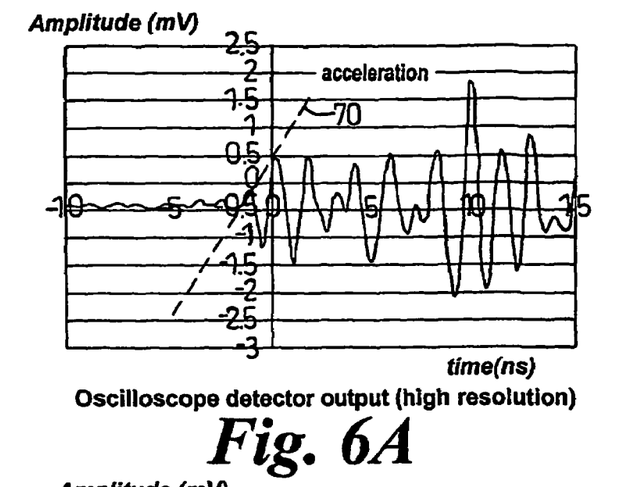
FIGS. 6A, 6B and 6C are illustrations of typical thermoelastic response wave forms using the excitation and detection systems of FIG. 5C.
Figure 6B:
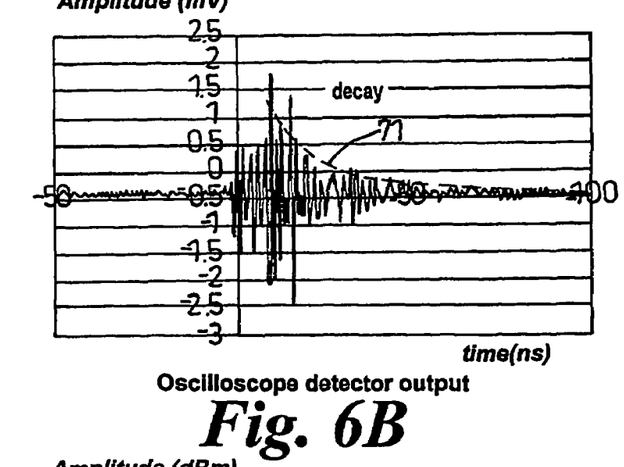
Figure 6C:
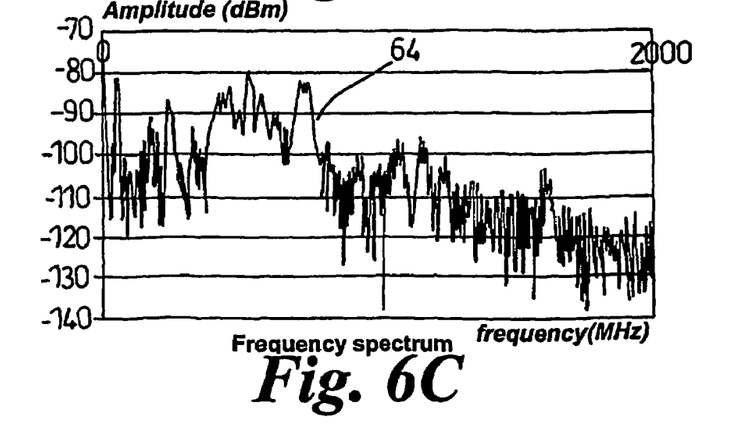

The frequency and amplitude of the acoustic wave in the probe structure and thus of the induced signal current, is a function of the physical and/or chemical properties of material 33 bound to the surface of the probe structure 30. Thus, if the mass or other physical and/or chemical properties of the material 33 bound to the surface of the probe structure 30 changes, a consequent change in the amplitude and frequency of the current 35 is observed. As described below this can be monitored on an oscilloscope. FIG. 6A shows the thermoelastic response signals including the initial response when the excitation laser beam strikes the probe structure. FIG. 6B indicates the decay of the stored acoustic energy in the probe structure, while FIG. 6C is the Fourier Transform of the received thermoelastic response signal indicating the various frequency components that are stimulated.

Changes that occur to the physical and/or chemical properties of the material bound to the probe structure can be detected by the detection system 15. If the excitation response is initially measured for the probe structure with the probe material 33 bound thereto, and is then measured again after exposure of the probe material to the sample 16, any changes to the physical and/or chemical properties of the material binding to the surface of the probe structure will be indicated, e.g. quantitatively, by the magnitude of change in the excitation response.

Figure 4:
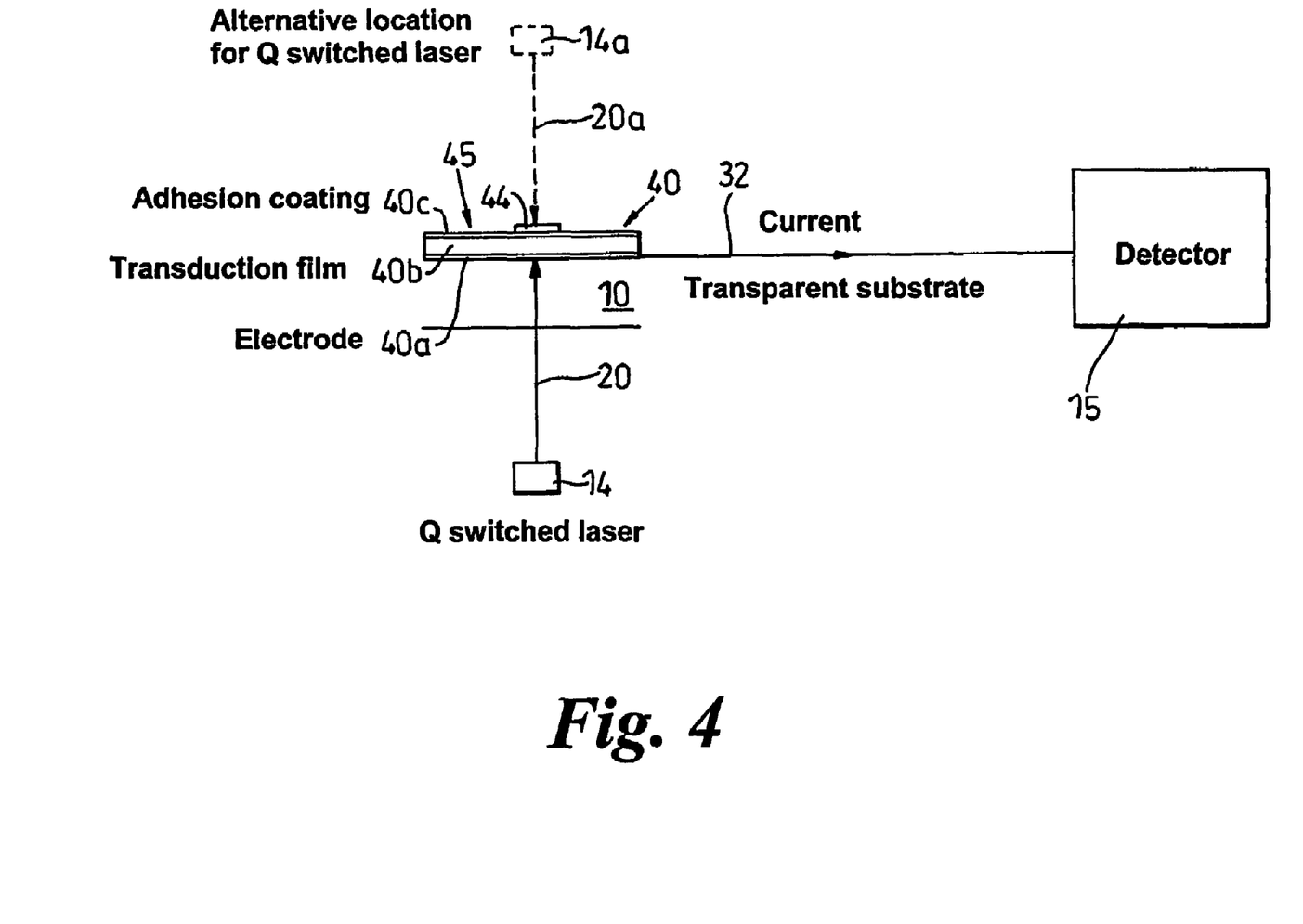
FIG. 4 is a schematic diagram illustrating a further embodiment of the invention using a laser based excitation system and a thin film transducer detection system.

With reference to FIG. 4 an alternative embodiment of the probe structure, excitation system and detection system will now be described. Like the arrangement of FIG. 3 this embodiment also generates an electrical response to the excitation beam. In this arrangement the probe structure 40 is formed on a thin optically transparent substrate 10. The probe structure is a layered structure comprising an electrode 40a formed on the substrate, a transduction film 40b formed thereon, and an adhesion coating 40c on top; the coating 40c being such as to facilitate binding of probe material 44 thereto.

The optical excitation beam 20, 20a in this instance (and some other instances) may alternatively be directed from above the substrate, shown at 14a. The excitation beam 20, 20a is directed onto the probe structure 40, and the resulting thermoelastic, thermoelectric and/or thermomagnetic response of the transduction film 40b generates a detectable electrical output via the electrode 40a.

An infrared emission output by the probe structure can be detected by a transduction film 40b that is a pyroelectric film. An acoustic emission by the probe structure can be detected by the electrode, e.g. a metal film electrode, 40a. In the case of a thermomagnetic excitation response the transduction film 40b could be a magnetoresistive layer that changes its resistance according to the magnetic field emission from the probe structure.

In common with the system of FIG. 2 the infrared, acoustic, magnetic or charge emission response of the probe structures vanes as a function of the physical and/or chemical properties of the material binding to the surface of the probe structure. If the mass bound to the surface of the probe structure increases a changed, usually a greater, emission response is observed.

In the preferred embodiments, the transducer element provides for a direct electrical pickup of signal current therefrom. In an alternative embodiment the signal pickup could be remote, e.g. by electromagnetic induction. For example the piezoelectric transducer can provide an electromagnetic signal that can be detected remotely by suitable antennae according to known principles.

Alternatively, charge emission can be detected by the electro-optical effect (Kerr, Pockels or Faraday) of an appropriate transduction film, which will change its refractive index and would be detectable as an optical signal according to known techniques.

With reference to FIGS. 5A to 5D four alternative arrangements of excitation and detection systems are described.

Figure 5A:
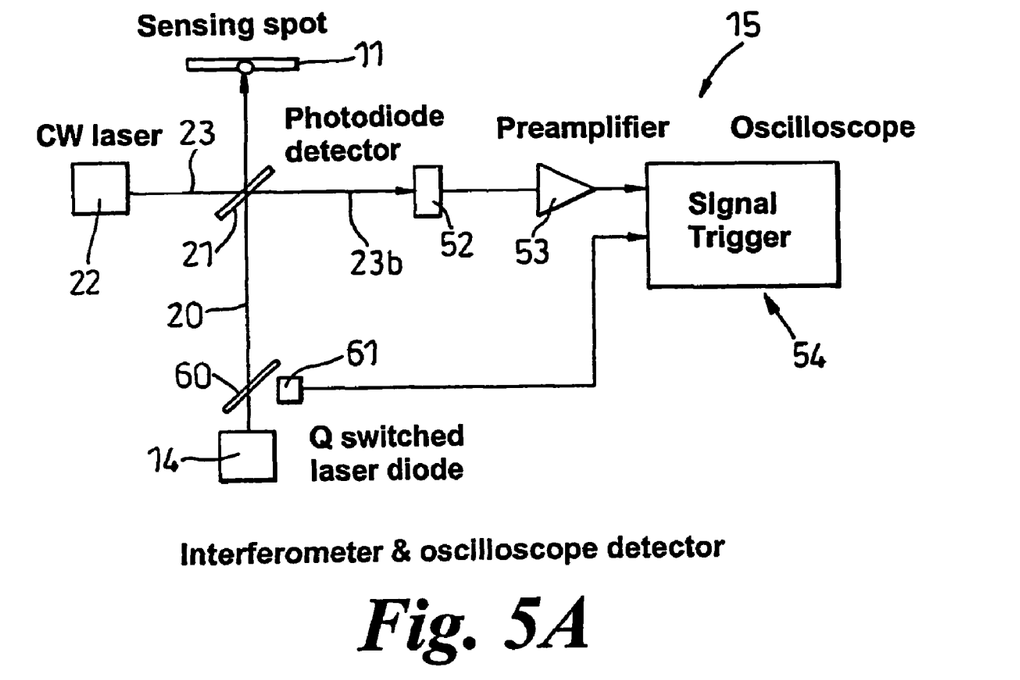
FIGS. 5A, 5B, 5C and 5D are schematic diagrams showing four different excitation and detection systems illustrating detection in both time and frequency domains.

FIG. 5A shows a digital oscilloscope detection system. This is the preferred system for the probe structures of FIG. 2 as it can track precise dimensional or positional changes in the probe structure. The excitation beam 20 is generated using a Q-switched laser 14 producing either single emissions or being self-modulated at frequencies of several, e.g. 10 to 200, kHz according to well known techniques.

The detection (interference) beam 23b is directed to an optical detection system 15 comprising a photodiode 52, a preamplifier 53 and a digitising oscilloscope 54 which is triggered by an optical detector 61 adjacent to the Q-switched laser and optically coupled thereto by a beam splitter 60.

The excitation beam 20 can be modulated by signals of up to several kHz, e.g. 10 to 200 kHz. The probe structure 11 is exposed to the pulsed excitation beam 20 and increases in volume, e.g. by between about 0.1% and 10%. This leads to a change in phase and intensity in the detection beam 23b due to changes, e.g. interference, in the optical path, and in the beam area, this latter as a result of a change in the size of the probe structure. Typically, the acceleration of the lateral movement in the probe structure 11 is detectable from intensity changes in the detection beam 23b and corresponds to a mass change of material bound to the probe structure. Mass changes in the range $10^{-14}$ to $10^{-10}$ may be detectable in preferred embodiments. In addition reflection at the boundaries of the probe structure leads to a characteristic resonant decay that typically has a frequency of between 20 MHz and 200 MHz and a decay constant of between $10^2$ and $10^8$ $s^{-1}$. Any change of the material bound to the probe structure 11 changes the form of the decay.

It will be understood that the digitising oscilloscope may communicate the results with a suitable automated digital storage and processing system (not shown) for rapid assessment of many excitation responses from different probe structures on the substrate.

Figure 5B:
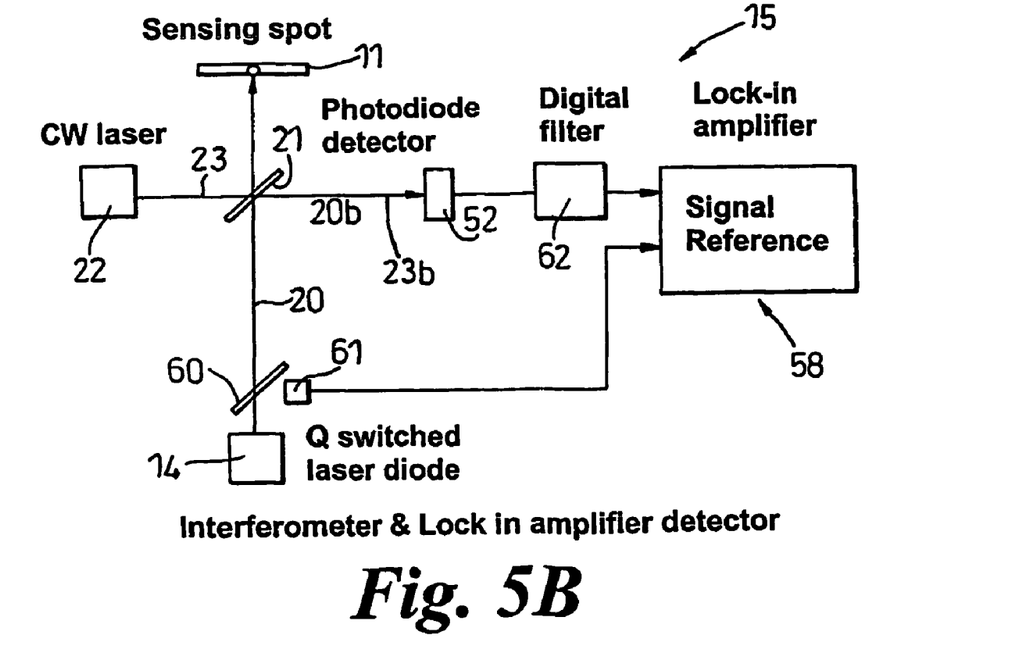

FIG. 5B shows a lock-in amplifier detection system 58 also suited to the probe structures of FIG. 2. Most components are similar to those described with reference to FIG. 5A as indicated by the common reference numerals, with the addition of the digital filter 62, which acts to reduce noise. In this case however the repeating output of a Q-switched laser 14 is used as a 10 to 200 kHz reference signal. The filter frequency is selected to the appropriate acoustic emission frequency of the probe structure in order to optimise the signal to noise ratio of the detection signal. The response frequency typically lies in the range 1 to 2000 MHz and deviates by a maximum of 10% when fragments 17 are adsorbed onto the probe structure 11.

Figure 5C:
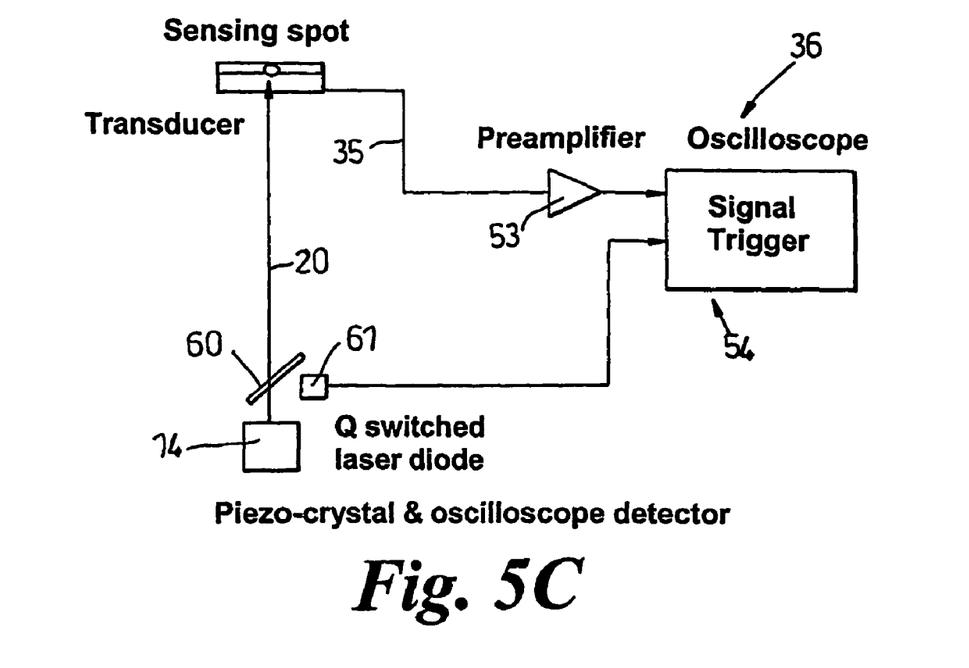

FIG. 5C shows an oscilloscope detection system 36 particularly adapted to the probe structures of FIG. 3 for direct detection of the thermoelastic response from the output signal current 35. In this system the Q-switched laser 14 produces the trigger signal (at optical detector 61) for the oscilloscope 36. The electrical detection signal (output signal 35) of the probe structure 30 is applied to the oscilloscope via preamplifier 53. The Fourier transform of the output signal produced by the pulsed laser 14 is used to determine more detailed characteristics of the fragments 17.

After adsorption of fragments 17 onto the probe material 13, changes in the frequency and time decay can be observed, and these changes can be used to evaluate the fragments 17 adsorbed on the probe structure, and hence the sample 16.

Figure 5D:
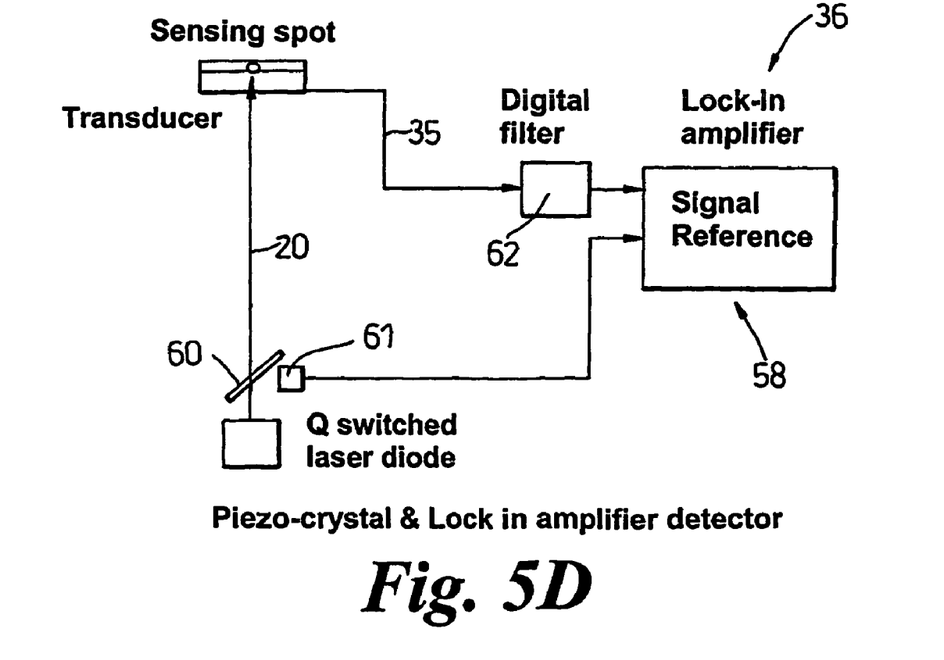

FIG. 5D shows an alternative synchronisation detection system that substantially filters the electrical emission signal 35 from the background noise using a digital filter 62. This eliminates noise from unwanted frequency ranges and allows higher gain amplification. The system coherently integrates the emission signal 35 from the transducer, averaging extraneous signals to zero.

In all the embodiments of FIGS. 5A, 5B, 5C and 5D typical signal voltage outputs are in the range 10 μV to 100 μV and offer sufficient sensitivity to detect, for example probe structure mass changes of $10^{-14}$ to $10^{-10}$ g.

An example of the electrical detection signal received from the electrode by the oscilloscope is shown in FIG. 6. FIG. 6A illustrates the excitation response of the probe structure to a pulsed excitation beam. The slope indicated at 70 provides a measure of the thermoelastic acceleration of the probe structures. FIG. 6B illustrates the excitation response of the probe structure to a single pulse excitation. The decay profile 71 provides a measure of the thermoelastic energy stored and released by the probe structure. FIG. 6C illustrates the frequency spectrum 64 of the excitation response of the probe structure.

Figure 7A:
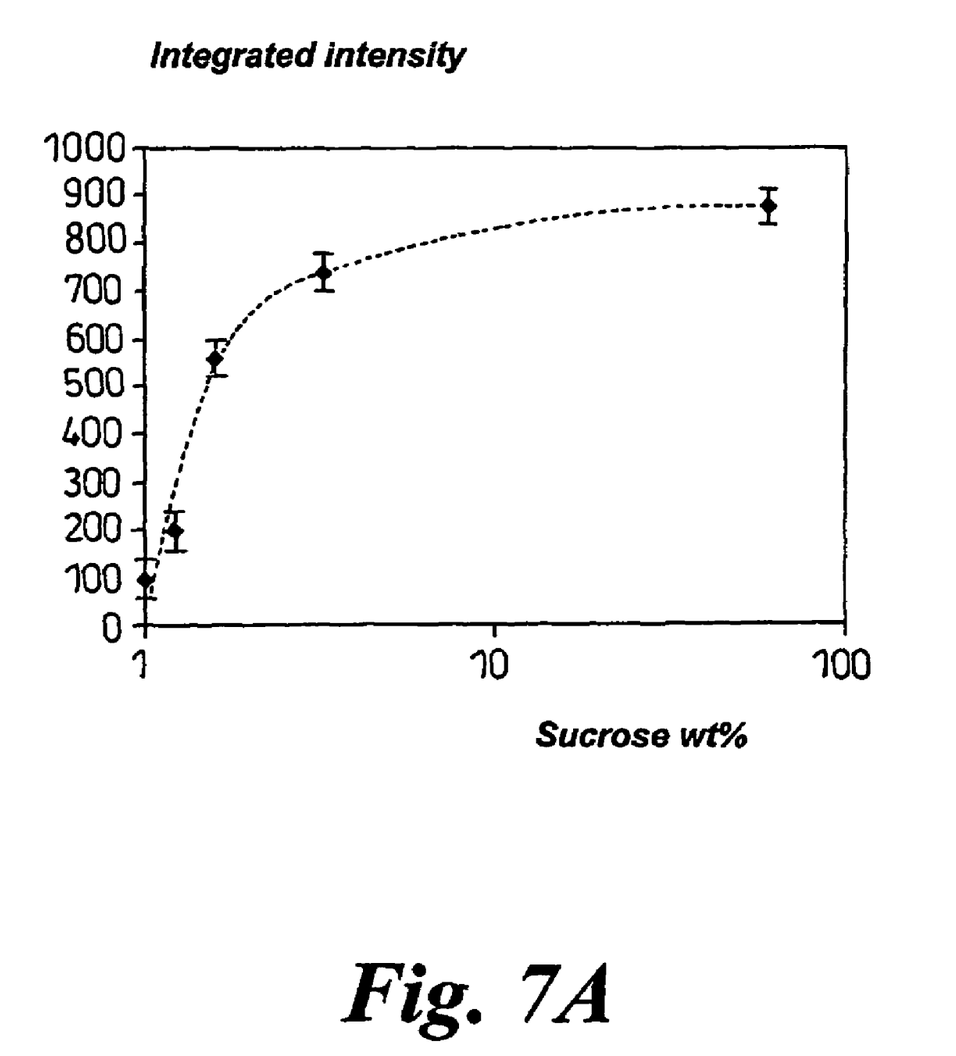
FIGS. 7A, 7B and 7C illustrate the response of the system of FIG. 5C to various reactions.

An exemplary characteristic response of the changes in thermoelastic response (vibration) of the probe structure before and after exposure to sucrose solutions is shown in FIG. 7A.

Figure 7B:
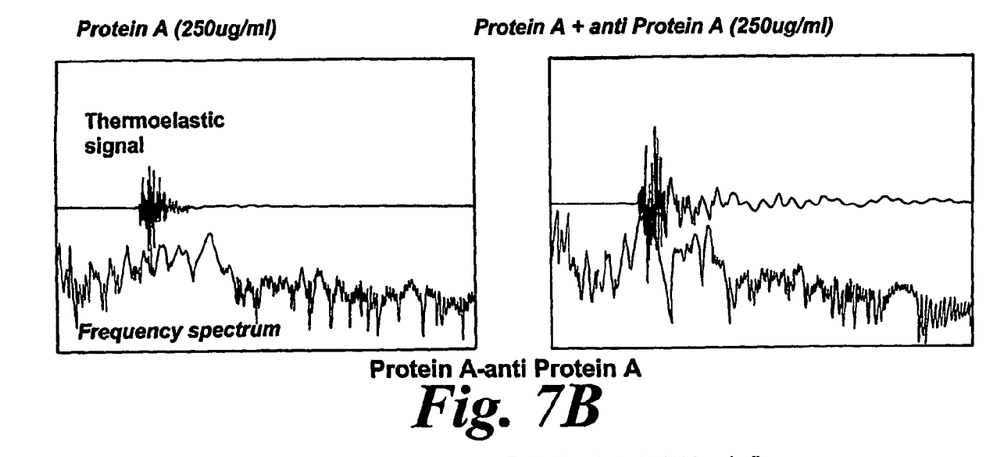
Figure 7C:
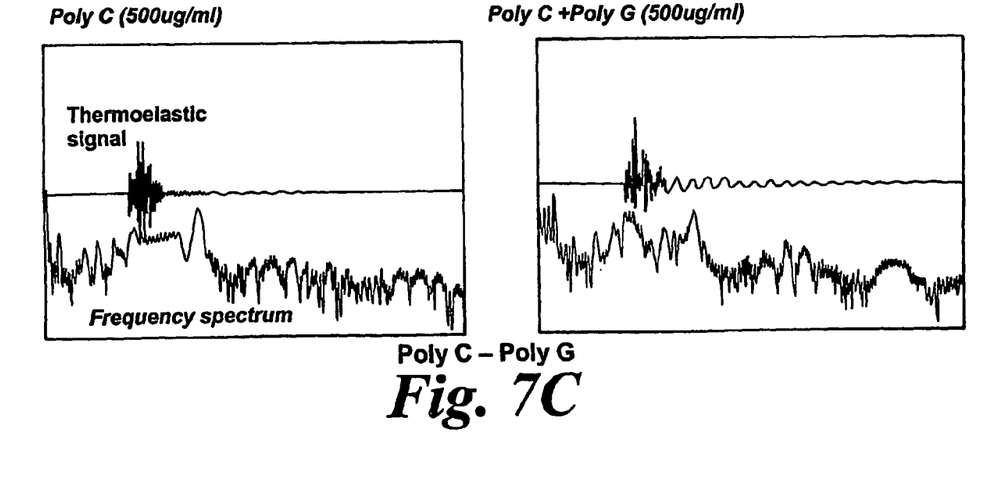

The effect of protein binding is shown in FIG. 7B and the effect of hybridisation of polynucleotides is shown in FIG. 7C.

The results shown in FIG. 7 were obtained at 25° C. using a 100 nm aluminium thermoelastic layer on a quartz substrate. The sucrose was dissolved in distilled water, and the protein and DNA solutions in PBS at pH 6.2. In FIGS. 7B and 7C Protein A and Poly C are used as the probe materials.

The upper curves are the time domain responses and the lower curves are the frequency domain responses. Significant changes in response are observed following these interface reactions.

Sample Delivery

Application of the sample to the probe structures may be achieved in a number of different ways. For DNA analysis the DNA sample may be extracted from whole blood. Separation of the DNA is carried out by dielectrophoretic field, which transports the cells to a contact electrode. An AC signal from 1 to 10 MHz source is applied to the contact electrode to provide a transport force. This removes the need for centrifuging the sample to separate the cells. With the cells at the electrode a voltage pulse is applied to lyse the cells breaking through the membrane and releasing the cell contents. Excision enzymes are used to cleave the genomic DNA strands to make sequenceable lengths similar to the length of an oligonucleotide on the probe structure. Temperatures above the annealing temperature-of the DNA are used to separate double strands and provide single strands for analysis. Exposure of the sample to the array of probe structures 11 may occur in a single step, especially for small array areas. We also contemplate multiple step exposure, e.g. by pipetting the sample onto each probe structure.

Coupling Chemistries

Probe materials 13, 33, 44, such as nucleic acids can be attached to the probe structures 11 of the acoustic transducer arrays using various suitable chemistries, of which the following is a non-exhaustive list of possibilities. The coupling chemistries are indicated for their preferred substrate type.

1. Avidin or streptavidin can be adsorbed to a gold surface, followed by oligonucleotides labelled with a biotin moiety which then binds irreversibly.

2. Amino-functionalised oligomers (3' and 5') can be attached to a silanised glass or silicon surface using glutaraldehyde.

3. Alkyl thiols can be attached to oligonucleotides and DNA. These thiols then assemble on a gold surface as an ordered monolayer film.

4. Carboxyl-modified surfaces of crystalline silicon will attach to thiol modified DNA by means of electrostatic adsorption of polylysine and a heterobifunctional cross-linker.

5. Aldehyde modified DNA oligonucleotides can be attached to a dextran acrylamide copolymer layer on glass, gold and silicon surfaces.

6. Alkoxysilanes such as aminopropyltriethoxysilane (APTES) are used to form a stable cross-linked film which is treated with succinic anhydride to modify the amino group to a carboxylic acid moiety. An amino acid linked nucleic acid will then bind via carbodiimide coupling.

7. 3-mercaptopropyltrimethoxysilane (MPS) can be used to attach thiol modified DNA.

8. Glycidoxypropyl-triethoxysilane (GOPS) will also attach a thiol modified DNA with a greater distance between the nucleic acid and the surface of the probe structure or substrate.

9. DNA/nucleic acid can also be conjugated to a silane for direct attachment to the probe structure surface.

10. Thiols attach the DNA to gold surfaces and silanes to silica surfaces.

The techniques and apparatus described above offer very considerable advantages in terms of reduced cost and complexity of analysis apparatus. Well known thin film lithographic or robotic spotting techniques can be used to form the high density arrays of probe structures, particularly on rotatable discs. Existing compact disc read/write technology can be used to provide the laser based excitation systems and disc access mechanisms for positioning the laser with respect to a rotating substrate. In such a system a drive means is provided for rotating the disc relative to an axis and an indexing means varies the position of the electromagnetic excitation and detection system relative to said axis, typically in a radial direction.

As a result the analysis apparatus can be made fully portable, being only a few kilograms in weight owing to the nature of the laser acoustic transducer. The analysis apparatus can be made largely or fully automatic designed for use by non-expert personnel, and does not require complex chemical protocols. This provides for highly reliable analysis. No special environment for use is required (e.g. Light- or sound-free), unlike fluorescent techniques, and the apparatus is found to be substantially noise free, being non-responsive to dust and optical contamination. Only material that is bound to the probe structures is detected.

The probe structure transducers formed on the substrates have been found to be sufficiently sensitive to enable detection of binding between DNA strands and single base-pair differences. The acoustic frequencies used can be adjusted to obtain further increases in sensitivity.

The probe structure transducer elements can be formed from any suitable material, particularly gold, silver, aluminium, copper or tungsten, by evaporation or sputtering with photolithographic patterning techniques well known in the semiconductor industry, to define the array.

The substrate can be formed from any suitable material, e.g. soda glass, BK7 glass, borosilicate glass, sapphire, silica glass (vitreosil), crystalline quartz or plastics materials such as polystyrene, polycarbonate or polyethylene.

Some applications of the systems described herein are in large molecule/small molecule interactions, large molecule/large molecule interactions, gaseous/solid interactions, genotyping, DNA sequencing and cell expression analysis.

Those skilled in the art will recognise that other embodiments not described above are within the scope of the appended claims.

The invention claimed is:

1. An apparatus for detecting a variation in a probe, comprising:
a sensor comprising a substrate and a plurality of thin film probe structures attached to a surface of the substrate, each probe structure being adapted to undergo a thermoelastic response when excited by temporally varying electromagnetic radiation, the thermoelastic response being a function of physical and/or chemical properties of the probe structure and a sample material binding thereto;
a source of electromagnetic radiation;
means for directing the electromagnetic radiation at each probe structure of the sensor; and
a transducer adapted to determine a thermoelastic response of each probe structure.

2. The apparatus of claim 1 wherein the sensor is in the form of a plate.

3. The apparatus of claim 1 wherein the substrate is electromagnetically transparent.

4. The apparatus of claim 1 wherein the substrate acts as, or is part of, the transducer.

5. The apparatus of claim 1 wherein the substrate is of such a thickness that the substrate has sufficient strength for ease of handling, and also that the substrate will permit a desired amount of electromagnetic radiation to pass through the substrate.

6. The apparatus of claim 5 wherein the substrate has a thickness in a range of 0.2 to 1.0 mm.

7. The apparatus of claim 1 wherein the sensor comprises a plurality of probe structures, each of the probe structures being adapted to undergo a localized electrical response when the probe structure is excited by temporally varying electromagnetic radiation and to generate an electrical output response corresponding thereto, characteristics of the electrical response being a function of physical or chemical properties of each probe structure and sample material binding thereto, and
a transducer for transmitting the electrical response.

8. The apparatus of claim 7 wherein different probe materials are bound to different probe structures.

9. The apparatus of claim 1 in which each probe structure has a substrate surface onto which is bound probe material.

10. The apparatus of claim 9 in which the substrate comprises a thin film.

11. The apparatus of claim 1 in which the plurality of thin film probe structures are formed in an array.

12. The apparatus of claim 1 in which each probe structure comprises probe material which is different from material of other probe structures.

13. The apparatus of claim 12 in which the probe material comprises molecules of one type.

14. The apparatus of claim 12 in which the probe material comprises a mixture of different molecules.

15. The apparatus of claim 1 in which a surface of the substrate is planar.

16. The apparatus of claim 1 in which a surface of the substrate is curved.

17. The apparatus of claim 1 in which the source of electromagnetic radiation emits radiation in the optical portion of the electromagnetic spectrum.

18. The apparatus of claim 1 in which the source of electromagnetic radiation comprises a laser.

19. The apparatus of claim 12 in which the source of electromagnetic radiation is positioned so that the radiation impinges directly on the probe material.

20. The apparatus of claim 12 in which the source of electromagnetic radiation is positioned so that electromagnetic radiation first passes through a substrate transparent to the electromagnetic radiation before impinging on the probe material.

21. The apparatus of claim 1 in which the source of electromagnetic radiation emits temporally varying electromagnetic radiation in the optical spectrum.

22. The apparatus of claim 21 in which the substrate is formed from an optically transparent medium, and in which the source of electromagnetic radiation is adapted to direct the electromagnetic radiation to a lower surface of a probe structure via the substrate.

23. The apparatus of claim 22 in which the probe structures are each adapted to absorb electromagnetic radiation to thereby generate a thermoelastic response in the form of a volume change within a probe structure, and in which the transducer comprises detecting means for detecting the volume change.

24. The apparatus of claim 1 in which each probe structure comprises a thin film metal spot.

25. The apparatus of claim 1 in which the transducer comprises receiving means for receiving reflected electromagnetic energy from a selected probe structure.

26. The apparatus of claim 22 in which the probe structures are each adapted to absorb electromagnetic radiation to thereby generate a thermoelastic response in the form of a lateral displacement of a corresponding probe structure, and in which the transducer comprises detecting means for detecting the lateral displacement.

27. The apparatus of claim 26 in which the probe structures each comprise a thin film dielectric material spot.

28. The apparatus of claim 1 in which the probe structures comprise a transducer element for generating an electrical output signal representative of a thermoelastic response of said probe structures.

29. The apparatus of claim 1 in which the source of electromagnetic radiation comprises a laser adapted to irradiate selected ones of the probe structures with pulsed or continuous wave electromagnetic radiation.

30. The apparatus of claim 1 in which the transducer comrises an optical interferometer for receiving a reference beam from an optical source, and an interference beam reflected from a probe structure.

31. The apparatus of claim 1 in which the transducer includes a transient recorder or digitizing oscilloscope for determining an amplitude and phase variation in thermoelastic response signals received from the probe structures.

32. The apparatus of claim 1 in which the source of electromagnetic radiation and the transducer include detecting means for detecting a change in resonant frequency of a selected probe structure.

33. The apparatus of claim 1 in which each probe structure includes an entrant electrode adapted to provide a ground plane to a lower surface of the substrate.

34. The apparatus of claim 1 further comprising a molecular probe material bound to an exposed surface of a probe structure.

35. The apparatus of claim 1 in which the substrate comprises a disc, and further comprising:
drive means for rotating the disc relative to an axis;
indexing means for varying a position of said electromagnetic excitation means and said detection means relative to said axis.

36. The apparatus of claim 2 in which the substrate comprises silica.

37. The apparatus of claim 2 in which the probe structures each comprise a thin film metal spot.

38. The apparatus of claim 2 in which the probe structures each comprise a thin film dielectric spot.

39. The apparatus of claim 2 in which each probe structure further includes a transducer element for generating an electrical output signal representative of the thermoelastic response of said probe structure.

40. The apparatus of claim 1 in which the probe structures are arranged in a series of generally circular or helical arrays on a circular disc substrate.

41. A method of using an apparatus,
   wherein the apparatus comprises:
      a sensor comprising a substrate and a plurality of thin film probe structures attached to a surface of the substrate, each probe structure being adapted to undergo a thermoelastic response when excited by temporally varying electromagnetic radiation, the thermoelastic response being a function of physical and/or chemical properties of the probe structure and a sample material binding thereto;
      a source of electromagnetic radiation;
      means for directing the electromagnetic radiation at each probe structure of the sensor; and
      a transducer adapted to determine a thermoelastic response of each probe structure; and
   wherein the method comprises:
      providing a plurality of probe materials respectively attached to the plurality of thin film probe structures;
      exposing the thin film probe structures to a sample material to permit binding of material to surfaces of the thin film probe structures;
      using the source of electromagnetic radiation to direct electromagnetic energy at the thin film probe structures; and
      detecting changes in thermoelastic response of each thin film probe structure to the electromagnetic energy by comparing a thermoelastic response with and without exposure to the sample material.

* * * * *